United States Patent [19]

Boudreaux

[11] Patent Number: 4,675,193

[45] Date of Patent: Jun. 23, 1987

[54] CHEESE-FLAVORED SUBSTANCE AND METHOD OF PRODUCING SAME

[75] Inventor: Donald P. Boudreaux, San Pablo, Calif.

[73] Assignee: Borden, Inc., Columbus, Ohio

[21] Appl. No.: 546,777

[22] Filed: Oct. 31, 1983

[51] Int. Cl.[4] ............................................... A23C 9/12
[52] U.S. Cl. ...................................... 426/35; 426/37; 426/38; 426/36; 426/39; 426/43
[58] Field of Search ..................... 426/35, 37, 38, 41, 426/42, 49, 650

[56] References Cited

U.S. PATENT DOCUMENTS

| | | | |
|---|---|---|---|
| 3,729,326 | 4/1973 | Kasik | 426/650 |
| 3,975,544 | 8/1976 | Kosikowski | 426/35 |
| 4,119,732 | 10/1978 | Kratochvil | 426/35 |
| 4,500,549 | 2/1985 | Crossman | 426/650 |

FOREIGN PATENT DOCUMENTS

| | | | |
|---|---|---|---|
| 1240345 | 7/1971 | United Kingdom | 424/35 |
| 1326516 | 8/1973 | United Kingdom | 424/35 |

OTHER PUBLICATIONS

Rose-Economic Microbiology, vol. 7, Fermented Foods, (1982), Academic Press, pp. 148-153, 164-165, 172-175, 180-181 and 188-191.
Abstract of Japanese Patent No. 57-189638, by Derwent Service.

*Primary Examiner*—Sam Rosen
*Attorney, Agent, or Firm*—Frank E. Robbins; James R. Laramie; George P. Maskas

[57] ABSTRACT

A two-stage process for producing a cheese-flavored substance is claimed. A flavor development medium is fermented with a source of lipase/protease; the source of lipase/protease is inactivated and the flavor development medium is fermented by at least one lactic acid-producing microorganism which is thereafter inactivated. The source of lipase/protease is preferably a microorganism, especially *Candida lypolitica* ATCC 20234. The cheese-flavored substance produced by the process and foods containing the cheese-flavored substance produced by the process are also claimed.

47 Claims, No Drawings

CHEESE-FLAVORED SUBSTANCE AND METHOD OF PRODUCING SAME

FIELD OF THE INVENTION

The invention relates to a two-stage process for making a substance having a cheese flavor utilizing a source of lipase, protease or both, at least one strain of lactic acid-producing bacteria and a flavor development medium having from about 0.3% to about 12% protein and from about less than 2% to about 85% fat. The flavor development medium containing fats and a source of non-fat milk solids is fermented for a period of time by the source of lipase/protease then inactivated. The inactivated flavor development medium is subsequently fermented by at least one lactic acidproducing microorganim. A relatively low solids cheese-flavored substance is produced. The low solids cheese flavor may be concentrated to 95% solids in dry powdered form or concentrated into a paste form in a range of between 40 and 75% solids.

BACKGROUND OF THE INVENTION

The production of cheese by traditional methods is a time-consuming process. The starting material for such traditional cheeses invariably is whole milk or whole milk that has either been augmented with milk fat or treated to separate high milk fat-containing fractions which are used for the production of cheese from relatively lower milk fat-containing fractions. The production of cheese having good flavor by such traditional methods is a complex process that is not well understood. What is understood, however, is that the flavors that give the various cheese their distinctive characteristics are gradually produced during ripening times which may vary from 2-3 months to well over one year at controlled temperatures. Because of the long and exacting storage conditions for the ripening process such traditionally produced cheeses are an expensive delicacy for a small segment of the cheese-consuming population.

An alternative approach to the production of cheeses having a distinctive and pleasing flavor is to obtain a cheese flavored substance, via various processes, having a distinctive cheese flavor and to add this cheese-flavored substance to a relatively young cheese, i.e., one that has not been subjected to a long aging process, or to a chesse that has not developed a distinctive flavor. Such cheese-flavored substances, of course, have a more general application in the food industry. They may be used to impart a cheese flavor to a variety of foods, including: processed cheeses, which include natural cheese, color, salt and emulsifiers; processed cheese foods which include, in addition to the ingredients of processed cheese, certain optional ingredients such as skim milk, whey, milk cream, albumin and skim milk cheese; or processed cheese spreads which include, in addition to the ingredients in processed cheese food, gums and the like for water retention. Cheese-flavored substances furthermore may be used to impart a distinctive cheese flavor to imitation cheese. Moreover, such distinctive cheese flavors can be used in a number of non-chesse type foods. For example, they can be used in baked goods such as cheese-flavored crackers, chips, breads, cakes, and the like.

In general, cheese-flavored substances may be produced by one of two methods, In the first method, a traditionally produced unripened cheese having no distinctive flavor is subjected to enzymatic digestion. The digest is combined with various ingredients and added to the food product to be produced. Although it is possible to produce relatively large amounts of cheese-flavored substances by this general process, it has the distinct disadvantage of a relatively expensive starting material.

A second approach to producing cheese flavor is to employ fermentative techniques. Cheese-flavored substances produced by processes of this type have almost always used substrates having relatively high milk fat concentrations—on the order of between 30% and 80% on a solids basis. Usually, such high milk fat substances take the form of cream or butter. In general, these processes all utilize substrates having relatively low protein concentrations, usually not exceeding 3% on a weight/volume basis. Although it is possible, using these conventional fermentation processes, to produce substances having distinct cheese tastes in a relatively short period of time—on the order of 2-5 days—these conventional techniques have the distinct disadvantage of requiring relatively expensive starting materials as substrates. Moreover, these starting materials are subject to spoilage in short periods of time if not stored under proper conditions, usually requiring refrigeration. Thus, the substrates used in conventional techniques entail considerable expense in acquisition and storage.

SUMMARY OF THE INVENTION

The process for producing the cheese-flavored substance according to the instant invention may be briefly described as a two-stage fermentation of a flavor development medium. The components of the two-stage fermentation are a source of lipase or protease or lipase and protease (herein referred to as lipase/protease), and at least one lactic acid-producing microorganism and a flavor development medium.

The flavor development medium generally will comprise fats in a range of from less than 0.5% (wt/vol) to about 50% (wt/vol) and protein from about 0.3% (wt/vol) to about 12% (wt/vol). Diary substances such as skim milk, whole milk, non-fat dry milk, whey, whey protein concentrate and the like can be used. Alternatively or additionally, animal milk (e.g., goat milk), milk fat, or vegetable oils containing fatty acids may also be used.

It is preferred that the source of lipase/protease is a lipase/protease-producing microorganism. The lipase/protease-producing miroorganism(s) may be produced in two steps. In the first step of the two steps, the inoculum development step, the lipase/protease-producing organism(s) is grown for a period of time in aerobic conditions in a complete inoculum development medium. In the second of the two steps an aliquot of the inoculum development medium containing the lipase/protease-producing organism(s) is placed in a first starter development medium and is cultured under aerobic conditions for a period of time.

After the first starter development medium containing the lipase/protease-producing microorganism has reached a predetermined growth point, the first stage of the two-stage fermentation is initiated by inoculating an aliquot of the lipase/protease-producing microorganism in the first starter development medium into the flavor development medium. The flavor development medium if fermented for a period of time and the lipase/protease producing microorganism and enzymes are inactivated to terminate the first stage of the two-stage fermentaion. At the same time, at least one lactic acid-producing microorganism is grown anaerobically in a second starter development medium for a period of time. The second stage of the two-stage fermentaion is initiated by inoculating an aliquot of the second starter development medium containing the lactic acid-producing microorganisms into the previously inactivated flavor development medium. After a period of time, the medium is again heat-inactivated. The process is described in further detail hereinbelow.

DETAILED DESCRIPTION OF THE INVENTION

The process according to the subject invention is a two-stage fermentaion of a flavor development medium utilizing a source of lipase/protease and at least one lactic acid-producing microorganism. The sources of lipase and protease may be any purified or partially purified preparations of lipase and protease. Such purified and partially purified sources of enzyme are readily available commercially. Alternatively, the process according to the invention is a two-stage fermentation of a flavor development medium by, as the source of lipase/protease, a lipase/protease-producing microorganism and at least one lactic acid-producing microorganism. The term "lipase/protease-producing microorganism" as used herein is intended to include: any lipase-producing microorganism, preferably any extracellular lipase-producing microorganism; any protease-producing microorganism, preferably an extracellular protease-producing microorganism; a combination of lipase-producing microorganism and protease-producing microorganism; or any lipase- and proteaseproducing microorganism. The choice of lipase/protease-producing microorganism will depend upon the contents of the flavor development medium.

The process according to the invention also encompasses a two-stage fermentation of a flavor development medium in which the source of lipase/protease is a purified or partially purified preparation of lipase/protease and a lipase/protease-producing microorganism. Thus, within the scope of the invention are fermentations of a flavor development medium in which the source of lipase/protease may be a purified or partially purified protease and a lipase-producing microorganism, a purified or partially purified lipase and a protease-producing microroganism; or a lipase- and protease-producing microorganism supplemented with a purified or partially purified lipase or protease or both.

Preferaby the lipase/protease-producing microorganism will be nonpathogenic, and particularly nonpathogenic to man. In particular, microorganisms such as—penicillium (especially *Penicillium roqueforti*), *Oidum lactis*, Cladisporum (especially *Cladisporum butaryl*), *Micrococcus* and Candida (especially *Candida lipolytica*) are suitable microorganisms. Preferred in the process according to the present invention is *Candida lipolytica* and in particular, *Candida lipolytica* deposited in the American Type Culture Collection, 12031 Parklawn Drive, Rockville, Md. 20852-1776 USA under the accession numbers ATCC 8661, ATCC 20320 and ATCC 20324. Especially preferred is *Candida lypolytica* ATCC 20324.

As mentioned above, at least one lactic acid producing microorganism is used in the two-stage fermentation according to the invention. Lactic acid producing microorganisms suitable for this purpose are desirably dairy strains of lactic acid producing organisms. Dairy strains of lactic acid producing microorganisms include the genuses Streptococcus (S.), Lactobacillus (L.), Leuconostoc (Le.), Micrococcus (M.), Citrobacter (C.) and Brevibacterium (B.). Within the genus Streptococcus, *S. cremoris, S. lactis, S. thermophilous* and *S. diacetilactis* are examples. Within the genus Lactobacillus, *L. casei, L. bulgaricus, L. acidophilous, L. delbrueckii,* and *L. helveticus* are examples. Within the genus Leuconostoc, *Le. cremoris, Le. dextranicum* and *Le. citrovorum* are examples. Within the genus Micrococcus, *M. caselytics, M. conglomeratus* and *M. freudenreichii* are examples. Within the genus Citrobacter, *C. intermedii* and *C. freudii* are examples. Within the genus Brevibacterium, *B. linens* is an example.

It is preferred in the process according to the invention, to use two lactic acid-producing microorganisms, and although any two of the above-listed lactic acid-producing microorganisms are usable, *S. lactis* and *L. casei* are preferred. Particularly preferred for the *S. lactis* is *S. lactis* strain $C_2$ kindly furnished by W. E. Sandine of Oregon State University at Corvallis, Oregon. Also preferred is *L. casei*, deposited in the American Type Culture Collection, 12301 Parklawn Drive, Rockville, Md., under accession number ATCC 39392.

The lipase/protease-producing microorganism(s) and lactic acid-producing microorganisms used in the two-stage fermentation according to the invention are separately developed for subsequent inoculation into the flavor development medium. The lipase/protease-producing microorganism(s) is developed for inoculation in two steps. Preferably this development is carried out under aerobic conditions. In the first of the two steps, the lipase/protease-producing microorganism(s) is inoculated into an inoculum development medium which is a complete medium suitable for growth of the lipase/protease-producing microorganism(s). Preferably, the complete medium will contain all the substances necessary for vigorous and sustained growth of the lipase/protease-producing microorganism(s). In general, such a medium will be a standard bacterial culture medium supplemented with yeast extract (Y). Examples of such media included but are not limited to Nutrient Broth (produced by Difco), Yeast Morphology Broth (Difco), Peptone (Difco), and Tryptocase Soy Broth (TSB) (Bethesda Biological Laboratories, hereinafter BBL). Yeast extract is available from Difco and Stauffer Chemical Company (hereinafter SCC) under the tradename KAT. Preferably, *Candida lipolytica* is inoculated into a three percent (%) TSB 1% Y medium and is grown aerobically for a period of time and at a temperature sufficient to yield a predetermined cell titre, generally between $10^6$–$10^9$ cells/milliliter (ml). A suitable temperature will range between 23°–35° C. 30° C. is preferred, at which temperature the first step of development will require from about 16 to about 18 hours.

In the second step of development of the lipase/protease-producing microorganism(s) for inoculation, an aliquot of the lipase/protease-producing microorganism(s), obtained at the end of the first step is inoculated into a first starter development medium and is cultured aerobically. The starter development medium may be any substrate that will support the vigorous growth of the lipase/protease-producing microorganism(s) and the production of lipase or protease or both lipase and protease. Such substrates include whole milk, non-fat dry milk (NFDM) resuspended in water, fluid skim milk, whey, concentrated whey, or dried whey (such as Teklac ®) (Formost) resuspended in water or dairy starter culture medium such as Insure ® (Hansens, Milwakee, Wis.). The foregoing starter development substrates may be used singly or in any combination. If NFDM is used, it is preferably resuspended in water to about 10% (wt/vol %). If concentrated whey or dried whey is used as the substrate, it is diluted or resuspended at a concentration of about 7% to about 15% (wt/vol %).

The inoculated first starter development medium is incubated at about 30° C. for 12 hours or until cell titres reach from about $10^8$ to about $5 \times 10^8$ cells/ml. During the incubation period the pH rises from about 6.4 to about 7.0. During incubation of the first starter development medium, lipase, protease or lipase and protease activity is monitored. Lipase activity in a range of about 11 units (U)/ml to about 30 U/ml is desirable. Preferably the lipase activity will be between about 20 U/ml and 26 U/ml as determined by using Lipase Test Kit No. 800B, available from Sigma Biochemicals, St. Louis, Mo.

Protease activity during the first starter development step is monitored by spectrophotometrically measuring the absorbance of soluble azure blue dye liberated by proteolysis of hide azure powder (Calbichem Catalogue #37716) by an aliquot of the first starter development medium.

Aliquots of the first starter development medium that has incubated to the extend desired are transferred into a flavor development medium which is described further hereinbelow. In general, the transfer of the first starter development medium containing the lipase/protease-producing microorganism(s) will be in a range of from about 3% to about 35% (wt/wt) of the flavor development medium. An inoculum of the first starter development medium of about 10% (wt/vol) is preferred.

The lactic acid-producing microorganisms are separately cultured in a second starter development medium which may be any dairy-starter medium suitable for the vigorous growth of the lactic acid-producing microorganisms. Examples of such dairy starter media include a product sold under the name In-Sure ® (Hansen's, Milwaukee, Wisconsin 53214), Funnel Grade (Miles Labs., Marschall Div., Wis.), MSM (Miles Labs., Marschall Div., Wisconsin), One-2-one (Miles Labs., Marschall Div., Wisconsin), T.S.S. (Dederich Corp., Germantown, Wis.), Phage Stat Complete (Pfizer, New York, N.Y.) and Phase 4 (Galloway West, Fond Du Lac, Wis.).

The lactic acid producing microorganisms are inoculated into the second starter development medium from slants and the medium is incubated for a sufficient period of time, generally between about 12 and 30 hours, at a sufficient temperature, generally in a range of between about 23° and about 35° C. to bring the second starter development medium to a pH from about 5.3 to about 5.5. Preferably, the incubation proceeds for about 20 hours at 30° C. at which time the cell titre for each of the lactic acid-producing microorganisms used will generally equal or exceed $10^8$ cells/ml. The duration of and temperature for the incubation of the second starter development medium can be varied as necessary so that the first starter development medium and second starter development medium are ready for transfer into the flavor development medium when needed.

In general, the transfer of the second starter development medium containing the lactic acid producing microorganisms will be in a range of from about 0.5% to about 5% (wt/vol). An inoculum of the second starter development medium of about 1 to 2% (wt/vol) is preferred.

Generally, the flavor development medium is sequentially inoculated with transfers of the incubated first and second starter development media with an inactivation step between the two transfers. Thus, in the first stage, the flavor development medium is inoculated with a transfer of the first starter development medium containing the lipase/protease-producing microorganism. After a period of time the first stage is terminated by heat inactivation of the lipase/protease prior to addition of the lactic acid-producing microorganisms. In the second stage, the heat inactivated flavor development medium is inoculated with a transfer of the second starter development medium containing the lactic acid-producing microorganisms. After a period of time the second stage is also terminated by heat inactivation.

The flavor development medium may be comprised of skim milk, defined as milk having less than 2% milk fat, whole milk, non-fat milk solids including non-fat dry milk, whey and whey protein concentrate, butter, cream or any other dairy product acceptable by the Food and Drug Administration Standards for the making of processed cheese food. Furthermore, if the cheese-flavored substance is to be used in imitation cheese vegetable oils (preferably those including fatty acids of 10 carbons inclusive or less, for example coconut oil, palm oil and the like), casein and animal milk fats may be used.

The flavor development medium may have a fat content of from less than 2% to 50% on a weight/volume percent basis. The protein content will generally range from about 0.7% to about 12% (wt/vol) protein. Preferred is a flavor development medium comprising fats and non-fat milk solids.

In the first stage, the flavor development medium is fermented at a temperature and for a period of time sufficient to reduce the pH of the flavor development medium to pH between about 4.5 and about 5.5. If a temperature of 30° C. is used the fermentation time will range between about 8 to about 48 hours depending on the amount of fat in the fat in the flavor development medium. Lower fermentation temperatures require concomitantly longer periods of time. If the flavor development medium has a relatively high butter fat content (50% w/v), the butyric acid concentration of the flavor development medium may be monitored instead of or along with pH. A butyric acid concentration reaching from about 0.7% to 1.15% (wt/wt) is acceptable. A butyric acid concentration of about 1% is preferred.

When the proper pH or butyric acid concentration is reached, the first stage of the flavor development medium fermentation is terminated by heat inactivation at a temperature sufficiently high to inactivate any microganism(s), protease, lipase of all three. Generally, raising the temperature to about 85° C. for about 45 minutes is sufficient. Alternatively, the above-mentioned microorganisms and enzymes may be inactivated by exposing the flavor development medium to very high temperatures exceeding 100° C. for short periods of time.

The second stage of the flavor development medium fermentation may be terminated, after the desired period of time in a similar manner. In general, the second stage of the flavor development medium fermentation will require between 3.5 and 80 hours at temperatures between 4° C. and about 35° C.

A cheese-flavored substance is thus formed that may be spray dried, freeze-dried, concentrated, or kept in unconcentrated form. If spray dried, a solids content of about 95% is desirable. If concentrated, a paste consistency of from about 40% to about 60% solids is desirable. Such paste form of the cheese flavored substance may have a fat content range of from less than 2% to about 85%.

The spray dried product will have a fat content range of from less than 2% to about 55% of the solids and a protein content range of from about 1% to about 40% of the solids. In general, a protein content of from about 21% to about 38% and fat concentration of from less than about 2% to 40% is desirable in the spray dried product.

The cheese-flavored substance produced by the above-described process may be used as a cheese flavor in processed cheese foods, and processed cheese spreads or may be added to various foods including imitation cheese and cheese-flavored snack foods. In addition, butter fat may be added to the cheese-flavored substance before blending in the various foods. The process for producing the cheese-flavored substance and the cheese-flavored substance produced thereby will be better understood from the following examples which are intended by the inventor to be exemplary only and non-limiting.

EXAMPLE I

*C. lipolytica* ATCC 20324 was inoculated from a slant into an inoculum development medium comprised of 3% TSB, 1% Y and was incubated for 40 hours at 30° C.

Four liters (1) of a first starter development medium comprised of 20% NFDM (Difco) was divided into two 2 liter portions and each was placed in a 6 l flask and autoclaved for 20 minutes. After cooling, each of the flasks containing the first starter development medium was inoculated with a 10% transfer of incubated inoculum development medium containing *C. lipolytica* 20234 and was allowed to incubate for 40 hours at 30° C. with rotary agitation at 200 rpm. A flavor development medium comprising 750 g of salted butter was heated to 85° C. for 30 minutes in a 2 l flask, cooled, inoculated with 450 grams (g) of the incubated first starter development medium, and incubated for 48 hours at 30° C. with rotary agitation at 200 rpm. At the end of the 48 hour period the flavor development medium was removed from the flask and heat inactivated at 85° C. for 30 minutes.

A second starter development medium, comprising lactose broth supplied by Difco, 3.0 g/l beef extract, 5.0 g/l bacto-peptone, 5.0 g/l bacto-latose and having in addition 5.0 g/l lactose and 2.5 g/l casein was inoculated with *S. lactis* $C_2$ and incubated with aeration at 30° C. for 48 hours with rotary agitation at 200 rpm.

The previously inactivated flavor development medium was cooled to 30° C. and inoculated with a 2% transfer of *S. lactis* $C_2$ from the incubated at 30° C. for 3.5 hours with rotary agitation at 200 rpm. At the end of 3.5 hours the flavor development medium was divided into 6 equal portions and the bottles were cold stored at 4° C. for 72 hours. At the end of 72 hours, half the samples were heat inactivated at 95° C. for 30 minutes. The samples were then ripened at room temperature for 3 days.

The products so produced were designated 1H (heated) and 1NH (non-heated).

EXAMPLE II

A second fermentation product was prepared in the same manner as in Example I except for the following. A second starter development medium comprising 10% skim milk (Difco) and 0.5% yeast extract was inoculated with *S. cremoris* 134 and was incubated under the same conditions as Example I hereinabove.

The previously inactivated flavor development medium was cooled to 30° C., and inoculated with a 2% transfer of the second starter development medium. The sample was thereafter treated as in Example I hereinabove. The two samples so produced were designated 2H and 2NH.

EXAMPLE III

A third fermentation product was prepared as in Example I except for the following.

Five hundred milliliters (ml) of a second starter development medium having the same composition as the second starter development medium of Example I was inoculated with *Lactobacillus casei* TA101, ATCC 39392, and was grown at 30° C. with rotary shaking at 170 rpm for about 18 hours in a sealed screwtop flask.

The previously inactivated flavor development medium was inoculated with a 1% transfer of *L. casei* TA101 ATCC 39393 and a 1% transfer of *S. lactis* $C_2$ produced as in Example I. The sample was thereafter treated as in Example I hereinabove. The two samples so produced were designated 3H and 3NH.

EXAMPLE IV

A fourth fermentation product was prepared as in Example I except for the following.

One hundred ml of a second starter development medium comprising 10% NFDM or lactose broth (described in Example I hereinabove) was inoculated with *S. lactis diacetilactis* ATCC 11007 and incubated in a second flask at 30° C. under aerobic conditions with rotary agitation at 220 rpm.

The previously inactivated flavor development medium was inoculated with a 1% transfer of *S. lactis diacetalactis* ATCC 11007 and a 1% transfer of *S. lactis* $C_2$ produced as in Example I hereinabove. The two samples so produced were designated 4H and 4NH.

EXAMPLE V

A fifth fermentation product was prepared as in Example I except for the following.

The previously inactivated flavor development medium was inoculated with a 1% transfer of *S. lactis* prooduced as in Example I hereinabove and a 1% transfer of *S. cremoris* 134 produced as in Example II hereinabove. The sample was thereafter treated as in Example I hereinabove. The two samples so produced were designated 5H and 5NH.

EXAMPLE VI

A sixth fermentation product was prepared as in Example I except for the following.

The previously inactivated flavor development medium was inoculated with a 1% transfer of *S. cremoris* 134 produced as in Example II hereinabove and a 1% transfer of *L. casei* TA101 ATCC 39392 produced as in Example III hereinabove. The two samples so produced were designated 6H and 6NH.

EXAMPLE VII

A seventh fermentation product was prepared as in Example I except for the following.

The previously inactivated flavor development medium was inoculated with a 1% transfer of *S. cremoris* 134 produced as in Example II hereinabove and a 1% transfer of *S. lactis diacetilactis* produced as in Example IV hereinabove. The sample was thereafter treated as in Example I hereinabove. The two samples so produced were designated 7H and 7NH.

EXAMPLE VIII

The samples produced in Examples I–VII hereinabove were evaluated for taste in a process cheese spread loaf. The process cheese spread loaf comprised 64% barrel American cheese, which is an unaged cheese. No aged cheese was used in the process cheese spread loaf. The fermentation products were blended into the process chesse spread loaf at 2.5% (weight/weight) of the loaf. The evaluation of the samples reported below records taste impressions imparted to the cheese spread loaf by the fermentation products additional to any flavor inherent in the cheese spread loaf.

| Sample No. | Comments |
|---|---|
| 1NH | Weak, clean (slight lipolytic), slight-medium lipolytic odor. Slight cheese slight lipolytic flavor. |
| 2NH | Good overall, very slight bitter, medium intensity. Medium lipolytic odor. Strong lipolytic flavor note. |
| 3NH | Moderate intensity, good lipase level. Slight lipolytic odor. Slight to medium cheesy. Weak cheese aftertaste. |
| 4NH | Weak, clean. Slight-medium odor. Fairly well rounded. Slight lipolytic flavor. Slight-medium cheese flavor. |
| 5NH | Medium intensity, clean, good lipase, slight sour. Medium lipolytic odor. Slight-medium cheesy flavor. Slight lipolytic background. |
| 6NH | Good, high cheese intensity, good lipase level. Strong lipolytic odor. Medium plus flavor level. |
| 7NH | Bitter, slight soapy to unclearn. Highest flavor intensity. Strong lipolytic odor. Similar to 6NH. |
| 1H | Slight soapy. Slight lipolytic odor. Very slight lipolysis, mild to medium cheesy flavor. |
| 2H | Slight soapy. Slight-medium lipolytic odor. Medium-medium plus flavor level. Lipolytic flavor pronounced. |
| 3H | Smooth, creamy, lower lipase. Slight lipolytic odor. Medium cheesy flavor. |
| 4H | Similar to 3H, slight higher lipase. Very slight lipolytic odor. Similar to 3H. |
| 5H | Sour, slight soapy. Slight lipolytic odor. Medium flavor level. |
| 6H | Slight bitter, medium lipase flavor. Very slight lipolytic odor. Slight-medium cheesy flavor. Lipolytic. |
| 7H | Very slight bitter, otherwise smooth, balanced. Slight to medium lipolytic odor. Slight-medium cheese flavor. |

What is claimed is:

1. A method for producing an edible substance having a cheese flavor, that when added to a food, is capable of imparting its cheese flavor to the feed, comprising:
   (a) fermenting a dairy flavor development medium comprising a fat in an amount of from less than 0.5% weight by volume to about 50% weight by volume, and protein in an amount from about 0.3% weight by volume to about 12% weight by volume, with at least one microorganism source of lipase/protease that produces during said fermentation at least one enzyme selected from the group consisting of lipase and protease;
   (b) inactivating said microorganism;
   (c) incubating said fermented flavor development medium with at least one lactic acid-producing microorganism to effect lactic acid fermentation, and then
   (d) inactivating said lactic acid-producing microorganism, and
   (e) recovering from the thus-processed flavor development medium an edible substance having a cheese flavor.

2. The method of claim 1 wherein said microorganism source of lipase/protease is selected from the genus Candida.

3. The method of claim 2 wherein said Candida is *Candida lipolytica* ATCC 20324.

4. The method of claim 1 wherein said at least one lactic acid-producing microorganism is a dairy strain of microorganism.

5. The method of claim 4 wherein said dairy strain of microorganism is selected from the group of genuses consisting of Streptococcus, Lactobacillus, Leuconostoc, Micrococcus, Cirobacter and Brevibacterium.

6. The method of claim 5 wherein said Streptococcus is selected from the group consisting of *S. cremoris, S. lactis, S. thermophilous,* and *S. diacetilactis*.

7. The method of claim 5 wherein said Lactobacillus is selected from the group of consisting of *L. casei, L. bulgaricus, L. acidophilous, L. delbrueckii, L. helveticus*.

8. The method of claim 5 wherein said Leuconostoc is selected from the group consisting of *Le. cremoris, Le. dextranicum* and *Le. citrovorum*.

9. The method of claim 5 wherein ssaid Micrococcus is selected from the group consisting of *M. caselvtics, M. conglomeratus* and *M. freudenreichii*.

10. The method of claim 5 wherein said Citrobacter is selected from the group consisting of *C. intermedii, C. freudenii*.

11. The method of claim 1 wherein said at least one lactic-acid producing strain of microorganism comprises two different species of lactic acid-producing microorganisms.

12. The method of claim 11 wherein said two lactic acid-producing microorganism are selected from the genuses consisting of Streptococcus, Lactobacillus, Leuconostoc, Micrococcus and Brevibacterium.

13. The method of claim 12 wherein said Streptococcus is selected from the group consisting of *S. cremoris, S. lactis, S. tremophilous,* and *S. diacetilactis*.

14. The method of claim 12 wherein said Lactobacillus is selected from the group consisting of *L. casei, L. bulgaricus, L. acidophilous, L. delbrueckii. L. helveticus*.

15. The method of claim 12 wherein said Leuconostoc is selected from the group consisting of *L. cremoris, L. dextranicum* and *L. citrovorum*.

16. The method of claim 12 wherein said Micrococcus is selected from the group consisting of *M. caselytics, M. conglomeratus* and *M. freudenreichii*.

17. The method of claim 14 wherein said Citrobacter is selected from the group consisting of *C. intermedii, C. freudenii*.

18. The method of claim 14 wherein said two lactic acid-producing organisms are *Lactobacillus casei* and *Streptococcus lactis* $C_2$.

19. The method of claim 1 wherein said flavor development medium comprises at least one substance selected from the group consisting of skim milk, whole milk, non-fat dry milk, whey, whey protein concentrate, dried whey, butter, cream and milk fat.

20. The method of claim 19 wherein said flavor development medium comprises at least one substance selected from the group further consisting of vegetable oils including fatty acids of 10 carbon atoms inclusive or less, animal milk, animal milk fat and casein.

21. The method of claim 1 wherein said incubating step is carried out until the pH of said flavor development medium reaches from about 4.5 to about 5.5.

22. The method of claim 21 wherein said pH is about 5.

23. The method of claim 1 wherein the duration of said first fermenting stage is about 6 to about 48 hours.

24. The method of claim 1 wherein the duration of said first fermenting stage is about 48 hours.

25. The method of claim 1 wherein the duration of said second fermenting stage is about 3.5 to about 80 hours.

26. The method of claim 1 further including after the second fermentation stage the step of concentrating the fermented flavor development medium.

27. The method of claim 26 wherein said fermented flavor development medium is concentrated to a solids range of from 30-95% solids wt./wt. %.

28. The method of claim 26 wherein said fermented flavor development medium is concentrated to a paste with a solids range from about 40 to about 60% wt./wt.

29. The method of claim 26 wherein said fermented flavor development medium is concentrated to a solids content of about 95% solids wt./wt.

30. The method of claim 26 wherein said concentrating step is spray drying.

31. The method of claim 26 wherein said concentrating step is performed after the second inactivating step.

32. The method of claim 26 wherein said concentrating step is performed before said inactivating step.

33. The method of claim 26 wherein said concentrating step is performed simultaneously with said second inactivating step.

34. The method of claim 1 wherein said flavor development medium comprises less than about 2% fat and about 5% protein.

35. The method of claim 19 wherein said flavor development medium comprises about 0.3% protein and about 50% fat.

36. The method of claim 1 wherein said flavor development medium comprises about 3% protein and about 6.5% fat.

37. A process for producing an edible substance having a cheese flavor, that when added to a food, is capable of imparting its cheese flavor to the food, comprising:

fermenting in a dairy flavor development medium supplying fat and protein, with at least one microorganism source of lipase/protease selected from the genus Candida and producing at least one enzyme selected from the group consisting of lipase and protease;

inactivating said microorganism source of lipase/protease;

incubating said fermented flavor development medium with at least one lactic acid-producing microorganism to effect lactic acid fermentation, inactivating said lactic acid-producing microorganism, and then recovering an edible substance having a cheese flavor from said thus-processed flavor development medium.

38. The process of claim 37 wherein said microorganism from the genus Candida is *Candida lipolytica*.

39. The process of claim 38 wherein said flavor development medium is salted butter.

40. The process of claim 39 wherein said microorganism of the species *Candida lipolytica* is the strain *Candida lipolytica* ATCC 20324.

41. The process of claim 38 wherein said lactic acid-producing microorganism is *S. lactis* $C_2$.

42. The process of claim 38 wherein said lactic acid-producing microorganism is *L. casei*.

43. The process of claim 37 wherein said lactic acid-producing microorganism is *S. Lactic diacetilactis*.

44. The process of claim 38 wherein said lactic acid-producing microorganism is a mixture of *S. lactis* $C_2$ and *S. cremoris* 134.

45. The process of claim 38 wherein said lactic acid-producing microorganism is a mixture of *S. cremoris* 134 and *L. casei*.

46. An edible substance having a cheese flavor that when added to a food is capable of imparting its cheese flavor to that food, said substance having been produced by the process of claim 39.

47. A cheese-flavored food product comprising a food selected from the group consisting of process cheese, process cheese food, process cheese spread, imitation cheese, and baked goods, to which has been added an edible substance having a cheese flavor prepared in accordance with the process of claim 38.

* * * * *